United States Patent [19]

Jakobsen et al.

[11] Patent Number: 5,227,379
[45] Date of Patent: Jul. 13, 1993

[54] PIPERIDINE COMPOUNDS AND THEIR PREPARATION AND USE

[75] Inventors: Palle Jakobsen; Jorgen Drejer, both of Vaerlose, Denmark

[73] Assignee: Novo Nordisk A/S, Bagsvaerd, Denmark

[21] Appl. No.: 803,200

[22] Filed: Dec. 5, 1991

Related U.S. Application Data

[60] Division of Ser. No. 673,933, Mar. 22, 1991, Pat. No. 5,158,961, which is a division of Ser. No. 337,301, Apr. 13, 1989, Pat. No. 5,017,585, which is a continuation-in-part of Ser. No. 106,154, Oct. 8, 1987, Pat. No. 4,877,799.

Foreign Application Priority Data

Nov. 3, 1986 [DK] Denmark ............................. 5232/86
Jun. 25, 1987 [DK] Denmark ............................. 3234/87
Apr. 28, 1988 [DK] Denmark ............................. 2310/88

[51] Int. Cl.$^5$ ................ C07D 405/00; C07D 417/00; A61K 31/54; A61K 31/535
[52] U.S. Cl. .............................. 514/228.2; 514/233.8; 514/316; 514/321; 514/326; 544/61; 544/129; 546/193; 546/197; 546/207; 546/214
[58] Field of Search ........................ 544/61, 60, 129; 546/193, 197, 207, 214; 514/227.8, 228.2, 231.5, 233.8, 316, 321, 326

[56] References Cited

PUBLICATIONS

Appel. "Current Neurology" vol. 6, Chapter 5, pp. 107-108 (1987).
Sheardown, J. J. et al., Science 247, 571-574 (1990).

Primary Examiner—C. Warren Ivy
Assistant Examiner—Celia Chang
Attorney, Agent, or Firm—Gordon W. Hueschen

[57] ABSTRACT

Piperidine compounds having the formula

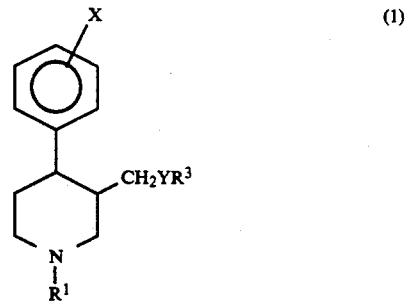

wherein
$R^3$ is 3,4-methylenedioxyphenyl, phenyl, or naphthyl which are optionally substituted with one or more halogen, $C_{1-6}$-alkoxy, or phenoxy, cyano, mono or poly halogenated $C_{1-6}$-alkyl, $C_{2-6}$-alkenyl, $C_{1-6}$-alkyl, or $C_{3-5}$-alkylene, $R^1$ is straight or branched $C_{1-8}$-alkyl substituted with piperidinyl morpholinyl thiomorpholinyl dioxolanyl or tetrahydrofuranyl, which heterocyclic radical is unsubstituted or $C_{1-6}$-alkyl substituted,
X is hydrogen, halogen, trifluoromethyl, hydroxy, cyano, or $C_{1-8}$-alkoxy,
Y is O or S; and pharmaceutically-acceptable acid addition salts thereof.

The compounds are useful in the treatment of anoxia, migraine, ischemia, and epilepsy.

14 Claims, No Drawings

PIPERIDINE COMPOUNDS AND THEIR PREPARATION AND USE

The present application is a division of our prior-filed copending application Ser. No. 07/673,933, filed Mar. 22, 1991, now U.S. Pat. No. 5,158,961, issued Oct. 27, 1992, which in turn is a division of our prior-filed copending application Ser. No. 07/337,301, filed Apr. 13, 1989, now U.S. Pat. No. 5,017,585, issued May 21, 1991, which in turn is a continuation-in-part of Ser. No. 106,154, filed Oct. 8, 1987, now U.S. Pat. No. 4,877,799, issued Oct. 31, 1989.

The present invention relate s to therapeutically active piperidine compounds, a method of preparing the same and to pharmaceutical compositions comprising the compounds. The novel compounds are useful in the treatment of anoxia, ischemia, migraine and epilepsy.

It is well known that accumulation of calcium in the brain cells (calcium overload) is seen after periods of uncontrolled hyperactivity in the brain, such as after convulsions, migraine, anoxia and ischemia As the concentration of calcium in the cells is of vital importance for the regulation of cell function, an uncontrolled high concentration of the cell calcium will lead to, or indirectly cause the symptoms and possibly also the degenerative changes combined with the above diseases.

Therefore calcium overload blockers selective for brain cells will be useful in the treatment of anoxia, ischemia, migraine and epilepsy.

Well known calcium antagonists such as nifedipine, verapamil and diltiazem have activity against pheripheral calcium uptake, e.g. in blood vessels and the heart, however have shown only very low activity against calcium overload in brain cells.

Accordingly it is an object of the invention to provide novel compounds having activity against calcium overload in brain cells. The novel compounds of the invention are piperidine compounds having the general formula I

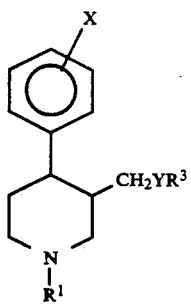

wherein
$R^3$ is 3,4-methylenedioxyphenyl, aryl or heteroaryl which are optionally substituted with one or more halogen, $C_{1-6}$-alkoxy, optionally substituted aryloxy or aryl-$C_{1-6}$-alkoxy, cyano, mono or poly halogenated $C_{1-6}$-alkyl, $C_{1-6}$-alkenyl, $C_{1-6}$-alkyl, $C_{3-5}$-alkylene or trifluoromethyl groups, $R^1$ is ,straight or branched $C_{1-8}$-alkyl unsubstituted or substituted with one or more cyano, ester, dialkylamino, hydroxy, amido, halogeno, substituted or unsubstituted piperidino, morpholino, thiomorpholino, dioxolanyl, tetrahydrofuranyl, $C_{1-8}$-alkoxy or $C_{3-8}$ cycloalkyl groups, X is hydrogen, halogen, trifluoromethyl, hydroxy, cyano or $C_{1-8}$-alkoxy, Y is O or S;

provided that $R^1$ is not unsubstituted $C_{1-8}$-alkyl, $C_{1-6}$-alkoxy-$C_{1-8}$-alkyl or $C_{3-8}$-cycloalkyl-$C_{1-8}$-alkyl, when $R^3$ is 3 4-methylenedioxyphenyl, aryl or heteroaryl optionally substituted with one or more $C_6$-alkyl, $C_6$-alkoxy, $C_{3-5}$-alkylene, $C_{3-8}$-cycloalkyl or aralkoxy, and at the same time X is hydrogen or halogen and salts thereof with a pharmaceutically acceptable acid.

Preferred compounds of formula I are compounds wherein, $R^3$ is 3,4-methylenedioxyphenyl, optionally substituted with halogen or $C_{1-6}$-alkoxy or phenyl substituted with $C_{3-5}$-alkylene, and/or $R^1$ is straight or branched $C_{1-8}$-alkyl, and/or X is hydrogen, halogen, trifluoromethyl or $C_{1-6}$-alkoxy.

Aryl is intended to mean carbocyclic aromatic rings, preferably phenyl.

Heteroaryl is intended to mean mono or fused dicyclio rings of up to 12 carbon atoms including one or more heteroatoms.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts.

The invention also relates to a method of preparing the above mentioned compounds. These methods comprise a) reacting a compound having the general formula II

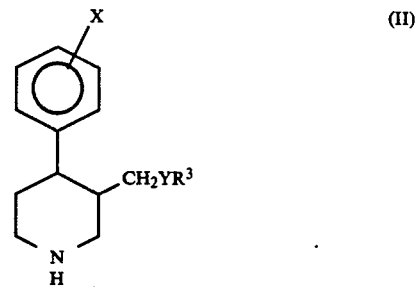

wherein $R^3$, X and Y have the meanings defined above, with a compound having the the general formula $R^1$-Z, wherein Z is a leaving group such as halogen and $R^1$ has the meaning defined above, or b) reacting a compound having the general formula III

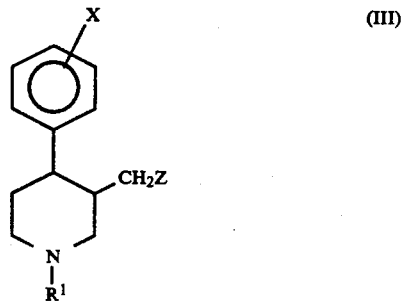

wherein $R^1$ and X have the meanings defined above, and Z is a leaving group, with a compound having the the general formula $R^3$-YH, wherein Y is O or S and $R^3$ has the meaning defined above, or c) reacting a compound having the general formula I,

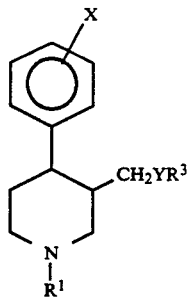

(1)

wherein X, $R^1$, $R^3$ and Y have the meanings defined above, with bromine, and optionally thereafter forming a salt with a pharmaceutically acceptable acid.

The pharmacological properties of the compounds of the invention can be illustrated by determining their capability to inhibit calcium uptake into brain synaptosomes.

PRINCIPLE

Depolarization of neuronal membranes leads to an opening of so-called 'voltage operated calcium channels' (VOC) in the membranes which allows a massive influx of calcium from the extracellular space. A crude synaptosomal preparation (so-called $P_2$ fraction) contains small vesicles surrounded by neuronal membrane and it is possible in such a preparation to study a depolarization-induced opening of VOC. In the present model $^{45}$Ca influx is induced in the synaptosomes by depolarization with elevated potassium concentrations, and the effect of test substances on this stimulated uptake is studied (Nachshen, D. A. and Blaustein, M. P., Mol. Pharmcol.,

ASSAY

A male Wistar rat is decapitated and the cerebral cortex removed and homogenized in 10 ml of ice-cold 0.32M sucrose using a glass homogenizer with a teflon pestle. All subsequent steps for isolation of synaptosomes are done at 0°–4° C. The homogenate is centrifuged at 1000×g for 10 min and the resulting supernatant is re-centrifuged at 18000×g for 20 min. This pellet ($P_2$) is resuspended in 0.32M sucrose (5 ml per g of original tissue) with a teflon pestle.

Aliquots (0.050 ml) of this crude synaptosomal suspension are added to glass tubes containing 0.625 ml of NaCl buffer (136 mM NaCl, 4 mM KCl, 0.35 mM $CaCl_2$, 1.2 mM $MgCl_2$, 20 mM Tris HCl, 12 mM glucose, pH 7.4) and 0.025 ml of various drug solutions in 48% Ethanol. The tubes are pre-incubated for 30 min on ice and then for 6 min at 37° C. in a water bath. The uptake is immediately initiated by adding 0.4 ml of $^{45}CaCl_2$ (specific activity=29–39 Ci/g; 0.5 Ci/assay), in 145 mM NaCl for non-depolarized samples and in 145 mM KCl for depolarized samples. The incubation is continued for 15 s.

The uptake is terminated by rapid filtration through GF-C glass fiber filters which are washed three times with 5 ml of a cold solution containing 145 mM KCl, 7 mM EGTA and 20 mM Tris HCl, pH 7.4. The amount of radioactivity on the filter disc is determined by liquid scintillation spectrometry.

TEST PROCEDURE

Test substances are dissolved in 10 ml of 48% ethanol at a concentration of 0.44 mg/ml. Dilution are made in 48% ethanol. Experiments are performed in quadruplicate. Controls for depolarized and nondepolarized samples are included in the assay and test substances are only tested in depolarized samples.

RESULTS

Test values are given as MEC (minimal effective concentration, μg/ml), which inhibit stimulated uptake of $^{45}$Ca significant different (P <0.05, Student's t-test) from control Test results obtained by testing some compounds of the present invention are given in the following table 1

TABLE 1

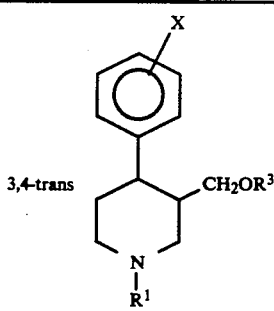

| $R^1$ | $R^3$ | X | OPTIC FORM | MEC μg/ml |
|---|---|---|---|---|
| —$(CH_2)_3CH_3$ | 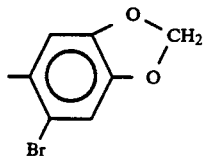 | 4-F | (−) | 0.3 |

TABLE 1-continued
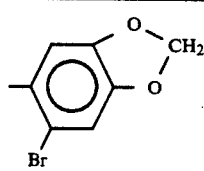
| R¹ | R³ | X | OPTIC FORM | MEC μg/ml |
|---|---|---|---|---|
| —(CH₂)₄CH₃ | 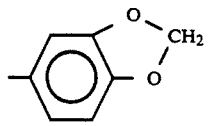 | H | (−) | 0.3 |
| —(CH₂)₄CH₃ | 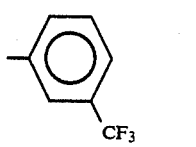 | 4-OCH₃ | (+−) | 1 |
| —CH₃ | 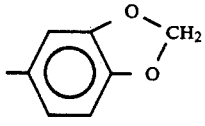 | H | (+−) | 1 |
| (CH₂)₄CH₃ | 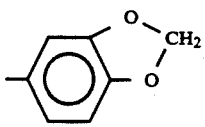 | H | (+−) | 1 |
| —(CH₂)₃—N⟨S⟩ | 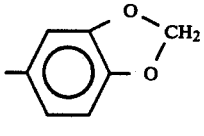 | 4-F | (−) | 0.3 |
| —CH₂—⟨tetrahydrofuran⟩ | 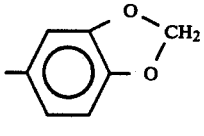 | — | (−) | 1 |
| —CH₃ | 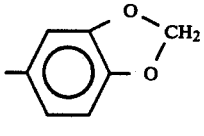 | 3-CF₃ | (+−) | 1 |
| —(CH₂)₃N⟨S⟩ | 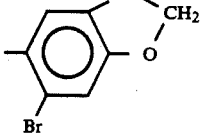 | 4-F | (−) | 1 |

TABLE 1-continued

[Structure: 3,4-trans piperidine with N-R¹, 3-position CH₂OR³, 4-position phenyl with substituent X]

| R¹ | R³ | X | OPTIC FORM | MEC μg/ml |
|---|---|---|---|---|
| —(CH₂)₄CH₃ | benzo[1,3]dioxol-yl (methylenedioxyphenyl) | 3-CF₃ | (+ −) | 0.3 |
| —(CH₂)₄CH₃ | benzo[1,3]dioxol-yl (methylenedioxyphenyl) | 4-O(CH₂)₄CH₃ | (+ −) | 0.3 |
| —(CH₂)₃CH₃ | phenyl with -CH₂CH=CH₂ and -OCH₃ | H | (+ −) | 0.3 |
| —(CH₂)₄CH₃ | benzo[1,3]dioxol-yl with Br | 4-F | (+) | 0.3 |

The compounds of the invention, together with a conventional adjuvant, carrier, or diluent, and if desired in the form of a pharmaceutically-acceptable acid addition salt thereof, may be placed into the form of pharmaceutical compositions and unit dosages thereof. In such forms they may be employed as solids, such as tablets or filled capsules, or liquids, such as solutions, suspensions, emulsions, elixirs, or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective calcium overload blocking amount of the active ingredient commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 0.05-100 mg in a pharmaceutically acceptable carrier per unit dosage.

The dosage of the compounds according to this invention is 0.1-300 mg/day preferably 10-100 mg/day when administered to patients, e.g. humans, as a drug.

A typical tablet which may be prepared by conventional tabletting techniques contains:

| Active compound | 5.0 mg |
| --- | --- |
| Lactosum | 67.8 mg Ph. Eur. |
| Avicel TM | 31.4 mg |
| Amberlite TM IRP 88 | 1.0 mg |
| Magnesii stearas | 0.25 mg Ph. Eur. |

Due to the high calcium overload blocking activity, the compounds of the invention are extremely useful in the treatment symptoms related to an accumulation of calcium in brain cells of mammals, when administered in an amount effective for blocking calcium overload in brain cells. The important calcium overload blocking activity of compounds of the invention includes both activity against anoxia, ischemia, migraine and epilepsy. The compounds of the invention may accordingly be administered to a subject, e.g., a living animal body, including a human, in need of a calcium overload blocker, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective calcium overload blocking amount, and in any event an amount which is effective for the treatment of anoxia, ischemia, migraine or epilepsy, traumatic head injury and neurodegerative diseases due to their calcium overload blocking activity. Suitable dosage ranges are 1-200 milligrams daily, 10-100 milligrams daily, and especially 30-70 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

(-)-trans-1-(2-cyanoethyl)-4-(4-fluorophenyl)-3-(3,4-methylenedioxyphenoxymethyl)-piperidine hydrochloride 1 g of (-)-trans-4-(4-fluorophenyl)-3-(3,4-methylene dioxyphenoxymethyl)-piperidine hydrochloride in 50 ml 99.9% ethanol was mixed with 3-bromopropionitrile (7 ml) and 2 g potassium carbonate. The mixture was refluxed for 70 h. After cooling 25 ml acetone and 25 ml diethylether were added, the precipitate filtered off, and the filtrate evaporated in vacuo. The residue was extracted with 1N NaOH/ether, the ether layer dried (MgSO$_4$) and evaporated to dryness The residue was dissolved in acetone and excess conc. HCl was added. Subsequent evaporation gave a hard glass, which was purified on a silica gel column using 99.5% ethanol as eluent. The title compound was isolated, and its structure confirmed by the IR and NMR data. M.p. 156° C.

The following compounds were prepared in the same manner from (-)-trans-4-(4-fluorophenyl)-3-(3,4-methylenedioxyphenoxymethyl)piperidine hydrochloride and the relevant halogeno compound (the actual halogen given). Oxalates were prepared from the free base by mixing equimolar amounts of amine and oxalic acid (anhydrous) in acetoe solution, which caused precipitation of the oxalate after few min at RT or in the fridge:

(-)-trans-1-(3-(4,4-dimethyl-1-piperidyl)-propyl)-4-(4-fluorophenyl)- 3-(3 4-methylenedioxyphenoxymethyl)-piperidine dihydrochloride from equimolar amounts of the "piperidine" and the chloro compound Reflux time 190 h, m.p. 267° C.

(-)-trans-1-(3-dimethylaminopropyl)-4-(4-fluorophenyl)-3-(3,4-methylenedioxyphenoxymethyl)-piperidine dihydrochloride, from the chloro compound by reflux for 50 h, a few crystals of iodine added. M.p. 295° C.

(-)-trans-4-(4-fluorophenyl)-3-(3,4-methylenedioxyphenoxymethyl)-1-(3-(2-methyl-1-piperidyl)propyl)-piperidine dihydrochloride, from equimolar amounts of "piperidine" and the chloro compound by reflux for 3 h, a few crystals of I2 added. M.p. 250° C.

(-)-trans1(2-ethoxycarbonylethyl)-4-(4-fluorophenyl)-3-(3,4methylene dioxyphenoxymethyl)piperidine oxalate, from the bromo compound, reflux time 2 h, m.p. 51° C., purified by column chromatography on silicagel using CH$_2$Cl$_2$/CH$_2$OH 9:1 as eluent.

(-)-trans-4-(4-fluorophenyl)-3-(3,4-methylenedioxyphenoxymethyl)-1-(3-thiomorpholinylpropyl)-piperidine dihydrochloride, from equimolar amounts of "piperidine" and the chloro compound, a few crystals I$_2$ added, reflux time 3 h, m.p. 267° C.

(-)-trans-1-carbamoylmethyl-4-(4-fluorophenyl)-3-(3,4-methylenedioxyphenoxymethyl)-piperidine hydrochloride, from the iodo compound, reflux for 2 h, m.p. 104° C.

(-)-trans-4-(4-fluorophenyl)-3-(3,4-methylenedioxyphenoxymethyl)-1-(3-morpholinopropyl)-piperidine dihydrochloride, from equimolar amounts of "piperidine" and the chloro compound, a few crystals of iodine added, reflux for 30 h, m.p. 108° C.

(-)-trans-1-(4-cyanobutyl)-4-(4-fluorophenyl)-3-(3,4-methylenedioxyphenoxymethyl)-piperidine oxalate, from the bromo compound by addition of a few iodine crystals and reflux for 1 h. The free bases was purified on a silicagel column using CH$_2$Cl$_2$/CH$_3$OH 9:1 as eluent m.p. 8° C.

(-)-trans-1-(1,3-dioxolyl-2-methyl)-4-(4-fluorophenyl)-3-(3,4-methylenedioxyphenoxymethyl)-piperidine oxalate, from the bromo compound, addition of one iodine crystal, reflux for 120 h, m.p. 53° C.

(-)-trans-4-(4-fluorophenyl)-1-tetrahydrofurfuryl-3-(3,4-methylenedioxyphenoxymethyl)-piperidine oxalate, from the bromo compound, reflux time 7 h, purified on silicagel column, eluent CH$_2$Cl$_2$/CH$_3$OH 9:1, hard glass. Identified by NMR and MS data. MS (m/e, % of base peak): 413,5; 343,38; 342,100; 204,25; 137,28; 109,38; 83,42: 58,100: 57,55.

(-)-trans-4-(4-fluorophenyl)-1-(6-hydroxyhexyl)-3-(3,4-methylenedioxyphenoxymethyl)-piperidine oxalate, from the chloro compound, addition of a few crystals of iodine reflux for 24 h, purified by column chromatography on silicagel CH$_2$Cl$_2$/CH$_3$OH 9:1 as eluent hard glass. Identified by IR, NMR and MS-data. MS (m/e, % og base peak): 429,3; 343,15; 342,55; 204,10; 171,10; 137,12; 109,15; 58,100.

(-)-trans-4-(4-fluorophenyl)-1-(3-hydroxypropyl)-3-(3,4-methylenedioxyphenoxymethyl)-piperidine oxalate, from the bromo compound, reflux 7 h, isolated as a hard glass, identified by IR and NMR.

EXAMPLE 2

(+-)-trans-1-methyl-3-(6-bromo-2-naphthoxymethyl)-4-phenylpiperidine hydrochloride 6-bromo-2-naphthol (2.45 g) was dissolved in MIBC (40 ml). NaOH (0.52 g) was added, and the mixture was stirred for ½ h. (+-)-trans-1-methyl-4-phenyl-3-phenylsulfonyloxymethylpiperidine (3.5 g) dissolved in MIBC (50 ml) was added to the "phenolate" solution heating to 110° C. for 6 h. The reaction mixture was evaporated to dryness and the residue extracted with OH/ether. The ether layer was dried (Na$_2$SO$_4$) filtered and evaporated to dryness. The crude product was purified on silicagel petrolether/CH$_3$OH 1:1 as eluent. The purified product was dissolved in ether and precipitated with excess conc. HCl-solution. Reprecipitation from acetone/ether gave 0.7 g compound, m.p.225° C.

In the same manner were prepared the following compounds from (+-)-trans-1-methyl-4-phenyl-3-phenylsulfonyloxymethylpiperidine and the appropriate substituted phenol or naphthol. Oxalates were prepared by mixing equimolar amounts of "piperidine base" and anhydrous oxalic acid in acetone solution.

(+-)-trans-1-methyl-3-(3-trifluoromethylphenoxymethyl-4phenylpiperidine oxalate. Heating at 130° C. until the sulfoester had reacted as seen by TLC. M.p. 92° C.

(+-)-trans-3-(4-chloro-1-naphthoxymethyl)-1-methyl-4-phenylpiperidine oxalate. Heating to 110° C. for 14 h. M.p. 88° C.

(+-)-trans-3-(4-allyl-2-methoxyphenoxymethyl)-4-phenylpiperidine oxalate. Reaction time 40 h at 110° C. M.p. 137° C.

(+-)-trans-1-methyl-3-(3-phenoxyphenoxymethyl)-4-phenylpiperidine oxalate. M.p. 166° C.

(+-)-trans-3-(2-cyanophenoxymethyl)-1-methyl-4-phenylpiperidine oxalate. M.p. 108°-110° C.

EXAMPLE 3

(+-)-trans-3-(3-trifluoromethylphenoxymethyl)-4-phenylpiperidine hydrochloride was prepared by means of alpha-chloroethyl chloroformate using the method described in J. Org. Chem. 49 (1984) 2081 (R. A. Olofson, J. T. Martz, J. P. Senel, M. Piteau and T. Malfroot). Na-dried toluene was used as solvent instead of 1,2- dichloroethane in the primary reaction. M.p. 171° C.

The following compounds were prepared in exactly the same manner by N-dealkylation of the corresponding N-methyl compound.

(+-)-trans-4-(4-methoxyphenyl)-3-(3,4-methylenedioxyphenoxymethyl)-piperidine. The hydrochloride was extracted with NaOH/ether, the above mentioned compound was precipitated from acetone/ether, m.p. 184° C.

(+-)-trans-3-(4-allyl-2-methoxyphenoxymethyl)-4-phenylpiperidine oxalate. The hydrochloride was extracted with OH$^-$/ether, the ether phase evaporated to dryness, and the residue dissolved in acetone and precipitated with an equimolar amount of anhydrous oxalic acid in acetone solution, m.p. 101° C.

(+-)-trans-3-(3-phenoxyphenoxymethyl)-4-phenylpiperidine oxalate. The hydrochloride was extracted with OH$^-$/ether, the ether phase evaporated to dryness, and the residue dissolved in acetone and precipitated by means of an equimolar amount of anhydrous oxalic acid in acetone solution. M.p. 138°-142° C.

EXAMPLE 4

The following compounds were prepared using the alkylation method described in example 1.

(+-)-trans-3-(3-trifluoromethylphenoxymethyl)-1-pentyl-4-phenylpiperidine oxalate, from (+-)-trans-3-(3-trifluoromethylphenoxymethyl)-4-phenylpiperidine and pentyl bromide by reflux for 10 h. M.p. 130° C.

(+-)-trans-4-(4-methoxyphenyl)-3-(3,4-methylenedioxyphenoxymethyl)-1-pentylpiperidine oxalate, from the corresponding unsubstituted piperidine and 1-bromopentane by reflux for 12 h, m.p. 213° C.

(+-)-trans-3-(4-allyl-2-methoxyphenoxymethyl)-1-pentyl-4-phenylpiperidine oxalate, by reflux of the corresponding unsubstituted piperidine with pentyl bromide for 16 h, m.p. 116° C.

(+-)-trans-3-(3,4-methylenedioxyphenoxymethyl)-1-pentyl-4-(3-trifluoromethylphenyl)-piperidine hydrochloride from the corresponding unsubstituted piperidine by reflux for 1 h with pentylbromide. M.p. 166.6° C.

(+-)-trans-1-pentyl-3-(3-phenoxyphenoxymethyl)-4-phenylpiperidine oxalate from the corresponding unsubstituted piperidine and pentylbromide by reflux for 2 h. M.p. 77° C.

(+-)-3-(4-allyl-2-methoxyphenoxymethyl)-1-pentyl-4-(3-trifluoromethylphenyl)-piperidine oxalate, prepared from 1bromopentane and 3-(4-allyl-2-methoxyphenoxymethyl)-4-(3-trifluoromethylphenyl)piperidine by reflux for 10 h. M.p. 130.4° C.

(+-)-3-(4-allyl-2-methoxyphenoxymethyl-1-pentyl-4-(4-trifluoromethylphenyl)-piperidine oxalate, prepared from the corresponding unsubstituted piperidine as the oxalate and pentylbromide, purified on silicagel column CH$_2$Cl$_2$/CH$_3$OH 9/1 as eluent. M.p. 141.2° C.

(+-)-trans-3-(4-allyl-2-methoxyphenoxymethyl)-1-butyl-4-phenylpiperidine oxalate. Preparation from 1-bromobutane and the unsubstituted piperidine by reflux for 5.5 h M.p. 74.9° C.

(+-)-trans-3-(4-allyl-2-methoxyphenoxymethyl)-1-cyclopropylmethyl-4-phenylpiperidine oxalate, from cyclopropylmethylbromide and unsubstituted piperidine by reflux for 2 h. M.p. 80.1 ° C.

(+-)-trans-3-(4-allyl-2-methoxyphenoxymethyl)-4-phenyl-1-propylpiperidine oxalate, from 1-bromopropane and unsubstituted piperidine by reflux for 6 h. M.p. 81° C.

(+-)-trans-3-(4-allyl-2-methoxyphenoxymethyl)-1-hexyl-4phenylpiperididne oxalate, from the corresponding unsubstituted piperidine and 1-bromohexane by reflux for 144 h. M.p. 114° C.

EXAMPLE 5

(+-)-trans-4-(4-methoxyphenyl)-1-methyl-3-(3,4-methylenedioxyphenoxymethyl)-piperidine, hydrochloride (+-)-trans-3-methoxycarbonyl-4-(4-methoxyphenyl)-1-methylpiperidine was prepared from arecoline and 4-bromoanisole as described by Plati et. al. (J. Org. Chem. 22 (1957) 261).

9.6 g of this compound was reduced with LiAlH₄ (2.8 g) in dry ether (150 ml), by reflux for 6 h, giving (+-)-trans-3-hydroxymethyl-4-(4-methoxyphenyl)-1-methylpiperidine (6.5 g) as an oil when the normal rinse-up procedure was used.

The crude product was dissolved in toluene (300 ml) triethylamine (7.7 ml) was added, and after stirring for ½h benzenesulphonyl chloride (4.3 ml) was added, and the mixture stirred at R. T. for 5 h.

The toluene phase was washed with H20, dried over MgSO₄, filtered and evaporated to dryness resulting in 7.9 g of (+-)-trans-4-(4-methoxyphenyl)-1-methyl-3-phenylsulfonyloxymethylpiperidine as a yellow oil.

4.1 g o±this oil dissolved in MIBC (200 ml) was added to a solution of sesamole (1.7 g) and NaOH (0.5 g) in MIBC (200 ml). The mixture was stirred at reflux temp. for 1.5 h. Subsequently the mixture was extracted with H₂O. The MIBC-phase was isolated and evaporated to dryness.

The resulting mass was extracted from aqueous NaOH/ether, the ether layer was isolated, dried over MgSO₄ and evaporated to dryness. The resulting oil was dissolved in acetone and precipitated as its hydrochloride salt by addition of excess conc. HCl-solution.

Yield 1.7 g of (+-)-trans-4-(4-methoxyphenyl)-1-methyl-3-(3,4-methylenedioxyphenoxymethyl)-piperidine, hydrochloride. M.p. 212.2° C. The identity was confirmed by the IR, NMR and MS-data.

(+-)-trans-1-methyl-3-(3,4-methylenedioxyphenoxymethyl)-4-(3-trifluoromethylphenyl)piperidine was prepared using the same reaction sequence starting from arecoline and 1-bromo-3-trifluoromethyl-benzene. M.p. 93.6° C.

EXAMPLE 6

(-)-trans-3-(2-bromo-4,5-methylenedioxyphenoxymethyl)-1-butyl-4-(4-fluorophenyl)-piperidine hydrochloride (-)-trans-1-butyl-4-(4-fluorophenyl)-3-(3,4-methylenedioxyphenoxymethyl)-piperidine hydrochloride (1 g) was dissolved in CH₂Cl₂ (50 ml). Bromine (0.124 ml) was added dropwise at R. T. After stirring for 2 h aqueous NaOH was added, and the CH₂Cl₂ layer was isolated, dried over Na₂SO₄ filtered and evaporated to dryness. The residue was dissolved in acetone excess conc. HCl was added, and the above mentioned bromo compound was precipitated by addition of ether. M.p. 116° C.

In exactly the same manner the following compounds were prepared from the corresponding unbrominated compounds.

(-)-trans-3-(2-bromo-4,5-methylenedioxyphenoxymethyl)-1-pentyl-4-phenylpiperidine hydrochloride, m.p. 156° C.

(-)-trans-3-(2-bromo-4,5-methylenedioxyphenoxymethyl)-4-(4-fluorophenyl)-1-pentylpiperidine hydrochloride. M p. 105° C.

(-)-trans-3-(2-bromo-4,5-methylenedioxyphenoxymethyl)-1-(3-dimethylaminopropyl)-4-(4-fluorophenyl)-piperidine dihydrochloride. M.p. 250° C. (d).

(-)-trans-3-(2-bromo-4,5-methylenedioxyphenoxymethyl)-4-(4-fluorophenyl)-1-(2-methoxyethyl)-piperidine hydrochloride. M.p. 65° C. (hard glass).

(-)-trans-3-(2-bromo-4,5-methylenedioxyphenoxymethyl)-1-cyclopropylmethyl-4-(4-fluorophenyl)-piperidine hydrochloride. M.p. 60° C. (hard glass).

(-)-trans-3-(2-bromo-4,5-methylenedioxyphenoxymethyl)-1-(2,3-dibromopropyl)-4-(4-fluorophenyl)-piperidine hydrochloride. The crude product was purified on silicagel using CH₂Cl₂/CH₃OH 9/1 as eluent. M.p. 108° C.

(-)-trans-3-(2-bromo-4,5-methylenedioxyphenoxymethyl)-4-(4-fluorophenyl)-1-(3-thiomorpholinopropyl)-piperidine dihydrochloride. The crude product was purified on silicagel using CH₂Cl₂/CH₃OH 9/1 as eluent. M.p. 241° C.

(+-)-trans-3-(2-bromo-4-(2,3-dibromopropyl)-6-methoxyphenoxymethyl)-4-phenylpiperidine hydrochloride. M/p/ 98.9° C. (hard glass).

(+)-trans-3-(2-bromo-4,5-methylenedioxyphenoxymethyl)-4-(4-fluorophenyl)-1-pentylpiperidine hydrochloride. M.p. 112.3°–113.3° C.

EXAMPLE 7

(+-)-1-methyl-3-(3,4-methylenedioxyphenoxymethyl)-4-(3-trifluoromethylphenyl)-piperidine 3-methoxycarbonyl-1-methyl-4-(3-trifluoromethylphenyl)piperidine was prepared as the cis/trans mixture from arecoline and 3-bromo-trifluoromethylbenzene as described (J. Org. Chem. 22 (1957) 261). The product was purified by vacuum distillation. B.p. 90°-110° C./0.7 mmHg.

19.2 g of this compound was reduced by means of LiAlH4 (4.85 g) in dry ether (325 ml) in an N₂-atmosphere by reflux for 4 h. After the normal rinse-up procedure followed by purification on a silica gel column using CH₃OH/CH₂Cl₂ (1/1) as eluent 13.2 g oil was isolated. Identified as a cis/trans mixture of 3-hydroxymethyl-1-methyl-4-(3-trifluoromethylphenyl)piperidine by means of ¹H-NMR.

The compound was dissolved in toluene (300 ml), triethylamine (13.5 ml) was added, and the mixture stirred for 1 h. Subsequently benzenesulphonyl chloride (7.5 ml) was added, and the mixture stirred at RT for 70 h. The toluene phase was extracted with H₂O; the separated aqueous layer was extracted with ether and the combined ether and toluene phases were dried with MgSO₄, filtered and evaporated to dryness giving 10.3 g of an oil.

5 g of the oil, which was identified as 1-methyl-3-phenylsulphonyloxymethyl-4-(3-trifluoromethyl)-piperidine by ¹H-NMR, was subsequently dissolved in MIBC (50 ml) and added to a solution of sesamol (1.9) and NaOH (0.5 g) in MIBC (150 ml). The mixture was refluxed for 2 h, stirred at RT overnight and extracted with H₂O. The MIBC-phase was evaporated to dryness, the residue was extracted with NaOH/ether, the ether layer separated acetone and conc. HCl (2 ml) was added resulting in a precipitate.

This was purified on a silica gel column using CHCl₂/CH₃OH 9/1 as solvent, yielding 1.1 g of (+-)-trans-1-methyl-3-(3,4-methylenedioxyphenoxymethyl)-4-(3-trifluoromethylphenyl)piperididne. M.p. 93.5° C. and 0.1 g of (+-)-cis-1-methyl-3-(3,4-methylene dioxyphenoxymethyl-4-(3-trifluoromethylphenyl)piperidine isolated as the oxalate identified by its ¹H-NMR and mass spectrum.

(+-)-3-(4-allyl-2-methoxyphenoxymethyl)-1-methyl-4-(3-trifluoromethylphenyl)piperidine oxalate was prepared from 1methyl-3-phenylsulphonyloxymethyl-4-(3- trifluoromethyl)piperidine and eugenol as described above by reflux for 1.5 h. M.p. 43.5° C.

EXAMPLE 8

(+-)-trans-3-(3,4-methylenedioxyphenoxymethyl)-1-pentyl-4-(4-pentyloxyphenyl)piperidine hydrochloride was prepared by refluxing 4-(4-hydroxyphenyl)-3-(3,4-methylenedioxyphenoxymethyl)piperidine hydrochloride (0.35 g) with 1-bromopentane (1.8 ml) and $K_2CO_3$ (1 g) in abs. ethanol (25 ml) for 2 h. The rinse-up procedure described in example 1 gave the title compound. M.p. 148.2° C.

EXAMPLE 9

(+-)-3-(4-allyl-2-methoxyphenoxymethyl)-1-methyl-4-(4-trifluoromethylphenyl)piperidine oxalate This compound was prepared by exactly the same reaction sequence as described in example 7 using arecolin and 4-bromotrifluorobenzene as the starting materials. The intermediates were identified by means of $^1$H-NMR and so was the identity of the product confirmed.

EXAMPLE 10

(-)-trans-4-(4-fluorophenyl)-3-(2-iodo-4,5-methylenedioxyphenoxymethyl)-1-pentylpiperidine oxalate (-)-trans-4-(4-fluorophenyl)-3-(3,4-methylenedioxyphenoxymethyl)1-pentylpiperidine (1.2 g) was dissolved in $CH_2Cl_2$ (50 ml). Silver trifluoroacetate (0.66 g) was added, followed by iodine (0.76 g) in $CH_2Cl_2$ added over a 10 min. period. Stirring for 24 h at R. T. The mixture was filtered, extracted with OH$^-$, the $CH_2Cl_2$-phase dried ($NaSO_4$) and subsequently evaporated to dryness. The residue was purified on silica gel and precipitated as the oxalate in acetone solution. M.p. 93.6°-94.0° C.

EXAMPLE 11

(+-)-trans-3-(4-propenyl-2-methoxyphenoxymethyl)4-(4-fluorophenyl)-1-pentylpiperidine oxalate 3-chloromethyl-4-(4-fluorophenyl)-1-pentylpiperidine (1 g) dissolved in dry DMF was added to a solution of eugenol (0.6 g) and sodium (0.99 g in abs. ethanol 50 ml. The mixture heated to 100° C. for 5 days. After 4 days NaH was added.

The reaction mixture was extracted with OH$^-$/ether, the etheral layer was dried ($MgSO_4$), evaporated to dryness and purified on a silica gel column using $CH_2Cl_2/CH_3OH$ as eluent. Precipitated as the oxalate from acetone solution. Identified by $^1$H and $^{13}$C NMR. M.p. 128.0°-128.4° C.

We claim:

1. A piperidine compound selected from those having the formula

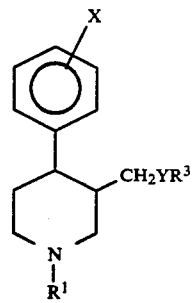

wherein
$R^3$ is 3,4-methylenedioxyphenyl, phenyl, or naphthyl which are optionally substituted with one or more halogen, $C_{1-6}$-alkoxy, phenoxy, or benzyloxy, cyano, mono or poly halogenated $C_{1-4}$-alkyl, $C_{2-6}$-alkenyl, $C_{1-6}$-alkyl, or $C_{3-5}$-alkylene,
$R^1$ is straight or branched $C_{1-6}$-alkyl substituted with piperidinyl, morpholinyl, thiomorpholinyl, dioxolanyl, or tetrahydrofuranyl, which may be unsubstituted or $C_{1-6}$-alkyl substituted,
X is hydrogen, halogen, trifluoromethyl, hydroxy, cyano, or $C_{1-8}$-alkoxy,
Y is O or S;
and pharmaceutically-acceptable acid addition salts thereof.

2. A compound of claim 1 wherein $R^3$ is 3,4-methylenedioxyphenyl, optionally substituted with halogen or $C_{1-6}$-alkoxy, or phenyl, substituted with $C_{3-5}$-alkylene.

3. A compound of claim 1 wherein X is hydrogen, halogen, trifluoromethyl, or $C_{1-6}$-alkoxy.

4. A compound of claim 1 wherein $R^3$ is 3,4-methylene dioxyphenyl, optionally substituted with halogen or $C_{1-6}$-alkoxy, or phenyl substituted with $C_{3-5}$-alkylene, and X is hydrogen, halogen, trifluoromethyl, or $C_{1-6}$-alkoxy.

5. A compound of claim 1 with is (-)-trans-4-(4fluorophenyl)-3-(3,4-methylenedioxyphenoxymethyl)-1-(3-thiamorpholinylpropyl)-piperidine dihydrochloroide.

6. A compound of claim 1, wherein the compound is (-)-trans-1-(3-(4,4-dimethyl-1-piperidyl)-propyl)-4-(4-fluorophenyl)-3-(3,4-methylendioxyphenoxymethyl)-piperidine or a pharmaceutically-acceptable salt thereof.

7. A compound of claim 1, wherein the compound is (-)-trans-4 -(4-fluorophenyl)-3-(3,4-methylenedioxyphenoxymethyl)-1-(3-(2-methyl-1-piperidyl)propyl)-piperidine or a pharmaceutically-acceptable salt thereof.

8. A compound of claim 1, wherein the compound is (-)-trans-4-(4-fluorophenyl)-3-(3,4-methylenedioxyphenoxymethyl)-1-(3-thiomorpholinylpropyl)-piperidine or a pharmaceutically-acceptable salt thereof.

9. A compound of claim 1, wherein the compound is (-)-trans-4-(4-fluorophenyl)-3-(3,4-methylenedioxyphenoxymethyl)-1-(3-morpholinopropyl)-piperidine or a pharmaceutically-acceptable salt thereof.

10. A compound of claim 1, wherein the compound is (-)-trans-1-(1,3-dioxolyl-2-methyl)-4-(4-fluorophenyl)-3-(3,4-methylenedioxyphenoxymethyl)-piperidine or a pharmaceutically-acceptable salt thereof.

11. A compound of claim 1, wherein the compound is (-)-trans-4-(4-fluorophenyl)-1-tetrahydrofurfuryl-3-(3,4-methylenedioxyphenoxymethyl)-piperidine or a pharmaceutically-acceptable salt thereof.

12. A compound of claim 1, wherein the compound is (-)-trans-3-(2-bromo-4,5-methylenedioxyphenoxymethyl)-4-(4-fluorophenyl)-1-(3-thiomorpholinopropyl)-piperidine or a pharmaceutically-acceptable salt thereof.

13. A calcium-channel antagonist composition comprising an effective calcium-uptake inhibitory amount of a compound of claim 1, together with a pharmaceutically-acceptable carrier or diluent.

14. A pharmaceutical composition according to claim 13 wherein it is in the form of an oral dosage unit containing 1-100 mg of the active compound.

* * * * *

UNITED STATES PATENT AND TRADEMARK OFFICE
CERTIFICATE OF CORRECTION

PATENT NO. : 5,227,379
DATED : Jul. 13, 1993
INVENTOR(S) : Palle Jakobsen, Jorgen Drejer It is certified that error appears in the above-indentified patent and that said Letters Patent is hereby corrected as shown below:

Title page, column 2, ABSTRACT, line 2; "(1)" should read
  -- (I) --.
Title page, column 2, "ABSTRACT" line 9, 10; "piperidinyl
  morpholinyl thiomorpholinyl dioxolanyl" should read
  --piperidinyl, morpholinyl, thiomorpholinyl,
  dioxolanyl,--.
Column 1, approximately line 14; "relate s" should read
  -- relates --.
Column 1, line 42; "(1) " should read -- (I) --.
Column 1, line 63; "$R^1$ is, straight" should read
  -- $R^1$ is straight --.
Column 2, line 6; "3 4-" should read --  3,4- --.
Column 2, line 7; "$C_6$-alkyl, $C_6$-alkoxy," should read
  -- $C_{1-6}$-alkyl, $C_{1-6}$-alkoxy --.
Column 2, line 48; delete "the" (second occurrence).
Column 2, line 50; move the comma "," from the begining
  of line 49 to the end of line 50 and insert after "Z".
Column 3, line 1; delete "the".
Column 3, line; 40 after "Pharmacol.," insert
  -- 16, 579 (1979)). --" (second occurrence).
Column 4, line 38; "significant" should read
  --significantly--.
Column 4, line 39; "control" should read --control.--.
Column 8, approximately line 52; "talo," should read
  -- talc, --.
Column 9, line 25, 26; move the period "." from the beginning of
  line 26 to the end of line 25 and insert after "epilepsy".
Column 9, line 42; "neurodegerative" should read
  -- neurodegenerative --.
Column 10, line 29; "12 added" should read --$I_2$ added--.
Column 10, line 30; "-trans1(" should read --trans-1-(--.

UNITED STATES PATENT AND TRADEMARK OFFICE
CERTIFICATE OF CORRECTION

PATENT NO. : 5,227,379
DATED : July 13, 1993
INVENTOR(S) : Palle Jakobsen, Jorgen Drejer It is certified that error appears in the above-indentified patent and that said Letters Patent is hereby corrected as shown below:

Column 10, line 49; "(4-fluorophenyI)" should read --
    --(4-fluorophenyl)--.
Column 10, line 54; "8° C." should read -- 89° C. --.
Column 11, line 17; "sulfonyloxymethyIpiperidine" should read
    -- sulfonyloxymethylpiperidine --.
Column 11, line 18; "solution heating" should read
    -- solution, heating --.
Column 11, line 34; "4phenylpiperidine" should read
    --4-phenylpiperidine--.
Column 12, line 4; "phenyIpiperidine" should read --
    -- phenylpiperidine --.
Column 12, line 37; "1bromopentane" should read
    --1-bromopentane --.
Column 12, line 59; "-4phenylpiperididne" should read --
    -- -4-phenylpiperidine --.
Column 13, line 17: "o±this" should read -- of this --.
Column 14, line 60; "piperididne." should read --piperidine--.
Column 14, line 68; "1methyl-" should read -- 1-methyl- --.

UNITED STATES PATENT AND TRADEMARK OFFICE
CERTIFICATE OF CORRECTION

PATENT NO. : 5,227,379
DATED : July 13, 1993
INVENTOR(S) : Palle Jakobsen, Jorgen Drejer It is certified that error appears in the above-indentified patent and that said Letters Patent is hereby corrected as shown below:

Column 15, line 67; after "formula" insert -- I --.

Column 16, line 1; "(1)" should read -- (I) --.
Column 16, line 18; "$C_{1-4}$-alkyl" should read -- $C_{1-6}$-alkyl, --.

Column 16, line 19; "$C_{1-6}$-alkyl" should read -- $C_{1-8}$-alkyl, --.

Column 16, line 35; "(4fluoro-" should read -- (4-fluoro- --.

Signed and Sealed this

Seventeenth Day of May, 1994

Attest:

BRUCE LEHMAN

*Attesting Officer*   Commissioner of Patents and Trademarks